(12) United States Patent
Zhu

(10) Patent No.: US 7,384,770 B1
(45) Date of Patent: Jun. 10, 2008

(54) RAPID QUANTIFICATION OF ACETIC ACID-PRODUCING BACTERIA USING REAL-TIME PCR

(75) Inventor: Xiangyang Zhu, Lake Zurich, IL (US)

(73) Assignee: Gas Technology Institute, Des Plaines, IL (US)

( * ) Notice: Subject to any disclaimer, the term of this patent is extended or adjusted under 35 U.S.C. 154(b) by 0 days.

(21) Appl. No.: 11/651,204

(22) Filed: Jan. 9, 2007

(51) Int. Cl.
*C12P 19/34* (2006.01)
*C07H 21/04* (2006.01)

(52) U.S. Cl. .................................. 435/91.2; 536/24.33

(58) Field of Classification Search ............... 435/91.1, 435/91.2
See application file for complete search history.

(56) References Cited

U.S. PATENT DOCUMENTS

| | | | |
|---|---|---|---|
| 6,812,339 B1 * | 11/2004 | Venter et al. ............. | 536/24.31 |
| 7,250,289 B2 * | 7/2007 | Zhou ....................... | 435/287.2 |
| 2005/0221439 A1 * | 10/2005 | Bakaletz et al. ........... | 435/69.3 |

OTHER PUBLICATIONS

Hongboa et al. Journal of American Sciencew, vol. 1,No. 3, pp. 1-47, 2005.*
Kim and Cha, Biotechnology and Bioengineering, vol. 83, No. 7, pp. 841-853, Sep. 2003.*
Turinsky et al. Journal of Bacteriology, vol. 180, No. 22, pp. 5961-5967, Nov. 1998.*
Ponchel et al., BMC Biotechnology, vol. 3, No. 18, pp. 1-13, Oct. 2003.*
Jennings and Tanner, Proceedings of the 2000 Conference on Hazardous Waste Research, pp. 299-306, Holiday Inn Denver Southeast, Denver Colorado, May 23-25, 2000.*
Buck et al. Biotechniques, vol. 27, pp. 528-536, Sep. 1999.*
Inglis, G. D. et al., "Direct Quantification of *Campylobacter jejuni* and *Campylobacter lanienae* in Feces of Cattle by Real-Time Quantitative PCR," *Applied and Environmental Microbiology*, vol. 70, No. 4, pp. 2296-2306, Apr. 2004.
Abbad-Andaloussi, S. et al., "Effect of Glucose on Glycerol Metabolism by *Clostridium butyricum* DSM 5431," *J. of Applied Microbiology*, 84, 515-522, 1998.
Bainotti, A.E. et al., "Growth Kinetics of *Acetobacterium* sp. on Methanol-Formate in Continuous Culture," *J. of Applied Microbiology*, 88, 191-201, 2000.
Broda, D.M. et al., "*Clostridium algidixylanolyticum* sp. nov., a psychrotolerant, xylan-degrading, spore-forming bacterium," *International Journal of Systematic and Evolutionary Microbiology*, 50, 623-631, (2000).

Chapelle, F.H. et al., "Microbial Acetogenesis as a Source of Organic Acids in Ancient Atlantic Coastal Plain Sediments," *Geology*, V. 24; No. 10; pp. 925-928, Oct. 1996.
Gibson, G.R. et al., "Regulatory Effects of Bifidobacteria on the Growth of Other Colonic Bacteria," *J. of Applied Bacteriology*, 77, 412-420, 1994.
Kanauchi, O. et al., "Increased Growth of *Bifidobacterium* and *Eubacterium* by Germinated Barley Foodstuff, Accompanied by Enhanced Butyrate production in Healthy Volunteers," *International Journal of Molecular Medicine*, 3, 175-179, 1999.
Louis, P. et al., "Restricted Distribution of the Butyrate Kinase Pathway Among Butyrate-Producing Bacteria from the Human Colon," *J. of Bacteriology* vol. 186, No. 7, pp. 2099-2106, Apr. 2004.
Montville, T.J. et al., "Influence of pH on Organic Acid Production by *Clostridium sporogenes* in Test Tube and Fermentor Cultures," *Applied and Environmental Microbiology*, vol. 49, No. 4, pp. 733-736, Apr. 1985.
Müller, Volker, "Minireview—Energy Conservation in Acetogenic Bacteria," *Applied and Environmental Microbiology*, vol. 69, No. 11, pp. 6345-6353, Nov. 2003.
Vetting, M. W. et al., "Structure of *Acinetobacter* Strain ADP1 Protocatechuate 3,4-Dioxygenase at 2.2 Å Resolution: Implications for the Mechanism of an Intradiol Dioxygenase," *Biochemistry*, 39, 7943-7955, 2000.
Zellner, G. et al., "*Anaerofilum pentosovorans* gen. nov., sp. nov., and *Anaerofilum agile* sp. nov., Two New, Strictly Anaerobic, Mesophilic, Acidogenic Bacteria form Anaerobic Bioreactors," *International Journal of Systematic Bacteriology*, vol. 46, No. 4, pp. 871-875, Oct. 1996.
Zhu, X. et al., "Characterization of Microbiol Communities in Gas Industry Pipelines,", *Applied and Environmental Microbiology*, vol. 69, No. 9, pp. 5354-5363, Sep. 2003.
Boynton, Z.L. et al., "Cloning, Sequencing, and Expression of Genes Encoding Phosphotransacetylase and Acetate Kinase from *Clostridium acetobutylicum* ATCC 824", *Applied and Environmental Microbiology*, vol. 62, No. 8, pp. 2758-2766, Aug. 1996.

* cited by examiner

*Primary Examiner*—Kenneth R. Horlick
*Assistant Examiner*—Cynthia Wilder
(74) *Attorney, Agent, or Firm*—Mark E. Fejer

(57) ABSTRACT

A set of primer pairs for amplifying a nucleic acid of an acetic acid-producing bacteria, each primer containing an oligonucleotide selected from the ackA gene region of the acetic acid-producing bacteria. The primers are particularly suitable for amplifying the nucleic acid of acetic acid-producing bacteria present in gas and oil production operations.

7 Claims, No Drawings

RAPID QUANTIFICATION OF ACETIC ACID-PRODUCING BACTERIA USING REAL-TIME PCR

BACKGROUND OF THE INVENTION

1. Field of the Invention

This invention relates to a method for the rapid detection and quantification of acetic acid-producing bacteria using real-time quantitative polymerase chain reactions (qPCR).

2. Description of Related Art

Microbiologically influenced corrosion is a significant problem affecting the gas and oil industry as well as other industries, and the monitoring of microbial populations within such industries is a component of overall corrosion control operations. Traditionally, the monitoring of microbial populations in samples obtained from gas and oil production operations has employed microbial growth tests. In such tests, samples are diluted to various levels and used to inoculate microbial growth media that is designed to favor the growth of various types of bacteria. After days to several weeks of incubation, the growth tests are scored based on the presence or absence of growth in these various microbiological media. Unfortunately, as numerous researches show, only about 0.1% to about 10% bacteria from environmental samples can actually grow in an artificial medium, and a significant portion of bacteria growing in the media are not actually the target bacteria. Therefore, growth tests are unable to provide the accurate quantification of target bacteria in the samples.

To circumvent problems associated with such growth-based methods, many culture-independent genetic techniques have been developed in the past decade and applied for the detection of pathogens and quality control and assurance of products in the medicine and food industries. Because many ecosystems, including pipeline systems, have a relatively low abundance of microorganisms, the polymerase chain reaction (PCR) has been widely used to amplify the genetic signals of microbes in complex environmental samples. However, traditional PCR-based methods are significantly biased by amplification efficiency and the depletion of PCR reagents. Real-time quantitative PCR (qPCR) has been developed and used in the last few years in the medical and food research/industries to detect and quantify a number of pathogenic or infectious microorganisms. Quantitative PCR has also been used to determine the abundance of microorganisms in many different types of complex environmental samples such as sediments, water, wastewater, and marine samples. The advantage of quantitative PCR over traditional PCR is that it provides more accurate and reproducible quantification of microorganisms because quantitative PCR quantifies PCR products during the logarithmic phase of the reactions. Moreover, quantitative PCR offers a dynamic detection range of six orders of magnitude or more, does not need post-PCR manipulation, and has the capability of high throughput analysis.

Acid-producing bacteria are present in a variety of environments, including oil- and gas-bearing formations, soils, and domestic, industrial, and mining wastewaters. Acid-producing bacteria produce organic acids such as acetic, butyric, formatic, lactic, succinic, and propionic acids, and contribute to metal corrosion.

While the total bacterial number in an oil or gas production sample indicates the general conditions for bacteria to grow in this unique environment, and, thus, the potential risk of microbial corrosion, some specific groups of microorganisms commonly found in such samples probably play a more important role in the corrosion process. One such microorganism is a acetic acid-producing bacteria which has been found to be present in environmental samples and, in particular, samples from gas and oil production operations.

SUMMARY OF THE INVENTION

Accordingly, it is one object of this invention to provide a quantitative polymerase chain reaction assay that can be used to rapidly detect and quantify the acetic acid-producing bacteria in environmental samples, including, but not limited to, gas and oil production operations samples.

The most abundant acid-producing bacteria found in gas and oil production environments are acetic acid-producing bacteria and butyric acid-producing bacteria. The gene ackA encodes the key enzyme acetate kinase α subunit, which along with phosphotransacetylase, catalyzes the conversion of acetyl coenzyme A to acetate. To address the above-stated object as well as other objects of this invention, a real-time qPCR assay has been developed by targeting the gene ackA encoding acetate kinase α subunits in acetic acid-producing bacteria. In one aspect, this invention features a set of PCR primer pairs that has been created to meet the specific requirements of real-time qPCR, which primer pairs amplify an approximately 104-bp DNA fragment from the ackA gene of acetic acid-producing bacteria. The creation of the specific PCR primers comprising the primer pairs was accomplished by determining the DNA sequences of ackA genes in acetic acid-producing bacteria most commonly found in gas and oil production operations. Each primer of the set of PCR primer pairs contains an oligonucleotide selected from the ackA gene region of the acetic acid-producing bacteria. The set of PCR primer pairs comprises forward primers, ackA-3F1 and ackA-3F2, having oligonucleotides selected from the group of SEQ. ID NOs 1 and 2, respectively, and reverse primers, ackA-4R1 and ackA-4R2, having oligonucleotides selected from the group of SEQ. ID NOs 3 and 4, respectively.

The set of PCR primer pairs of this invention has been evaluated in SYBR Green I real-time qPCR on reference acetic acid-producing bacteria strains as well as gas pipeline samples. The primer combination gives the best detection and quantification of acetic acid-producing bacteria commonly found in the oil and gas production operations. In addition to being appropriate for the real-time PCR quantification of acetic acid-producing bacteria, the set of primers of this invention is specific for samples from gas and oil production operations and combines high throughput with high analytical sensitivity and precision, offering a dynamic detection range of 6 orders of magnitude or more.

In another aspect, this invention features a method for quantifying the amount of acetic acid-producing bacteria in a sample from a gas and/or oil production environment in which a nucleic acid in the genome of the acetic acid-producing bacteria is amplified by quantitative PCR to form a double-stranded nucleic acid product, the nucleic acid product is contacted with a label, such as a fluorophore, e.g. SYBR Green I, in a solution for binding therebetween, and the acetic acid-producing bacteria is quantified by monitoring the signal produced by the bound label, the intensity of which is a function of the quantity of the ackA gene in acetic acid-producing bacteria in the sample.

DETAILED DESCRIPTION OF THE PRESENTLY PREFERRED EMBODIMENTS

Definitions

As used herein, the term "gene" means a DNA sequence containing information required for expression of a polypeptide or protein.

As used herein, the term "primer" refers to a single-stranded oligonucleotide that is extended by covalent bonding of nucleotide monomers during amplification or polymerization of a nucleic acid molecule.

As used herein, the term "template" refers to a double-stranded or single-stranded nucleic acid molecule which is to be amplified, synthesized or sequenced. In the case of a double-stranded DNA molecule, denaturation of its strands to form a first and the second strand is performed before these molecules may be amplified, synthesized or sequenced. A primer, complementary to a portion of a template is hybridized under appropriate conditions and a polymerase then synthesizes a molecule complementary to the template or a portion thereof.

As used herein, the term "amplification" refers to any in vitro method for increasing the number of copies of a nucleotide sequence with the use of a DNA polymerase. Nucleic acid amplification results in the incorporation of nucleotides into a DNA molecule or primer, thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include polymerase chain reactions, PCR, which may consist of 10 to 50 cycles of denaturization and synthesis of a DNA molecule.

As used herein, the term "oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

The invention disclosed herein is a PCR assay targeting the gene ackA encoding acetate kinase α subunit in acetic acid-producing bacteria using at least one of two novel forward primers, SEQ ID NOs 1 and 2, and using at least one of two novel reverse primers, SEQ ID NOs 3 and 4. The primers were designed based upon multiple alignments of partial sequences of the targeted ackA gene retrieved from GenBank and gas pipeline samples. BioEdit Sequence Alignment Editor, Version 5.0.9, was used for multiple alignments of sequences, and manual searches for alignments were also conducted to determine candidate primer sequences. All primers were checked for hairpin structure and dimmers using a free Oligonucleotide Analyzer (available at www.mature.com/oligonucleotide.html). MeltCal software, version 2.1 was then used to check the cross-hybridization among the sequences of primers used in some assay and calculate the melting temperature (Tm) using a nearest neighbor model. The sequences meet the general requirements of primer design for real-time quantitative PCR suggested by the RotoGene Real-Time PCR system manual provided by Corbett Research or in Inglis, G. D. et al., "Direct Qunatification of *Campylobacter jejuni* and *Campylobacter lanienae* in Feces of Cattle by Real-Time Quantitative PCR", *Appl. Environ. Microbiol.,* 2004. 70(4): pp 2296-2306. In addition, all primer sequences were analyzed for specificity using a BLAST SEARCH FOR SHORT, NEARLY EXACT MATCHES program and were found not to cross-react with any other non-target organisms.

The PCR primer pairs of this invention are based upon the DNA sequences of ackA genes from subsets of acetic acid-producing bacteria most commonly found in gas and oil production operations. Thus, the PCR primer pairs are ideally suited to accurately quantify acetic acid-producing bacteria in gas and oil production operations that have relevance to microbiologically influenced corrosion. If PCR primers were designed based on the DNA sequences of all known ackA genes published in DNA sequence databases such as GenBank, the regions of conserved sequences that are suitable for use in designing PCR primers would be more limited. Primers designed on the entirety of all ackA DNA sequences would by necessity fail to produce good yields from some ackA genes.

Not all species of acetic acid-producing bacteria are commonly present in gas and oil production environments. Thus, PCR primers that target the sequences of those bacteria most commonly encountered in gas and oil production environments yield superior results in developing real-time PCR methods to accurately quantify acetic acid-producing bacteria in these samples and are capable of detecting the target acetic acid-producing bacteria with the highest possible sensitivity. The quantification using the real-time PCR method and primers of this invention is achieved by measuring the fluorescent signal of SYBR-Green I dye resulting from its specific binding to the double-stranded amplified fragments.

The target acetic acid-producing bacteria for which the set of PCR primers of this invention are a perfect match include Bacillus anthracis str. 'Ames Ancestor' (AEO 17334), *Bacillus anthracis* str. Ames (AEO 17039), *Bacillus anthracis* str. Sterne (AE017225), *Bacillus cereus* ATCC 10987 (AE017279), *Bacillus cereus* ATCC 14579 (AE017013), *Bacillus cereus* E33L (CP000001), *Bacillus lichenformis* ATCC 14580 (CP000002), *Bacillus lichenformis* DSM 13 (AE017333), Bacillus subtilis acetate kinase (L17320), *Bacillus subtilis* rrnB-dnaB (AF008220), *Bacillus subtilis* subsp. *subtilis* str. 168 (Z99119) *Bacillus thuringiensis* serovar konkukian str. 97-27 (AEO 17355), *Clostridium acetobutylicum* ATCC 824 (AE007683), *Clostridium acetobutylicum* (U38234), *Staphylococcus aureus* MSSA476 (BX571857), *Staphylococcus aureus* subsp. aureus COL (CP000046), *Staphylococcus aureus* subsp. aureus Mu50 DNA (BA000017), *Staphylococcus aureus* subsp. aureus MW2 DNA (BA000033), *Staphylococcus aureus* subsp. aureus N315 (BA000018), and *Staphylococcus aureus* subsp. aureus MRSA252 (BX571856). All of these bacteria have the ackA gene.

In general, the PCR amplification process employed in the method of this invention may be carried out using procedures known to those skilled in the art, namely, denaturing, annealing, and elongation, which can be repeated as many times as necessary to produce the desired amount of the target nucleic acid. While the number of cycles may be affected by any of a number of factors, such as the nature of the sample, the number of cycles required to achieve the desired amplification in accordance with this invention is generally in the range of about 10 to about 50. However, cycles numbers outside of this range may be necessary and, thus, the statement of the above stated range is in no way intended to limit the scope of this invention.

As previously indicated, the set of PCR primers of this invention comprises two forward primers, ackA-3F1 (5'-GCA CCG CTT CAY AAT CC-3', melting temperature (Tm): 56.9-60.3° C., SEQ ID NO. 1), ackA-3F2 (5'-GCA CCR CTT CAY AAC CC-3', Tm: 56.3-63.0° C., SEQ ID NO. 2), and two reverse primers ackA-4R1 (5'-GTT TGG TGG AAT GCT GTA TC-3', Tm: 58.6° C., SEQ ID NO:3), and ackA-4R2 (5'-GTT TGA TGG AAT GCY GTA TC-3', Tm: 56.2-58.6° C., SEQ ID NO:4), all of which are perfect matches to the sequences of the above-mentioned acetic acid-producing bacteria. Thus, when this set of PCR primer pairs is used in the PCR amplification, only the above-mentioned acetic acid-producing bacteria are amplified. The primers, when used as pairs (at least one forward primer and at least one reverse primer), do not falsely amplify any bacteria which is not an acetic acid-producing bacteria. In addition, the primer pairs do not amplify sequences from Eukaryota, a high-level organism.

Example

A qPCR was performed using the primers of this invention, a Rotor-Gene 3000, 4 Channel Multiplexing, real-time PCR system (Corbett Research, Sydney, Australia), and a QuantiTect SYBR Green PCR kit (Qiagen, Inc., Valencia, Calif.). For quantification of the total bacteria, each 20 µL qPCR reaction contained 1× QuantiTect SYBR Green PCR Master Mix, 800 nM forward primer ackA-3F1, 1600 rtM forward primer ackA-3F2, 400 nM reverse primer ackA-4R1, and 800 nM reverse primer ackA-4R2, one µL of template, and 1.8 µL water. The cycling conditions consisted of 15 minutes of incubation at 95° C. followed by 35 cycles of 95° C. for 30 sec, 52° C. for 30 sec, and 73° C. for 30 sec for denaturing, annealing and elongation, respectively, followed by 70° C. for 30 sec, and 70° C. to 99° C. to generate melting curves.

Using *Clostridium acetobutylicum* genomic DNA (ATCC 824) as a template, the linear amplification range for the quantification of the acka gene was $1 \times 10^7$ to $1 \times 10^1$ copies per reaction (correlation coefficient, $R^2 > 0.9999$). The qPCR product size was 104 bp from position 355 to 458 of Clostridium acetobutylicum ATCC 824 ackA gene (complete genome GenBank Accession Number NC_003030, from 1891302 to 1892507).

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A set of primer pairs for amplifying a nucleic acid of an acetic acid-producing bacteria, each primer containing an oligonucleotide selected from the ackA gene region of said acetic acid-producing bacteria, wherein the first primer is an oligonucleotide selected from the group consisting of SEQ ID NO: 1 and SEQ ID NO: 2 and the second primer is an oligonucleotide selected from the group consisting of SEQ ID NO: 3 and SEQ ID NO: 4.

2. The primer pair of claim 1, wherein said acetic acid-producing bacteria is selected from the group consisting of *Bacillus anthracis* str. 'Ames Ancestor' (AE017334), *Bacillus anthracis* str. Ames (AEO 17039), *Bacillus anthracis* str. Sterne (AEO 17225), *Bacillus cereus* ATCC 10987 (AE017279), *Bacillus cereus* ATCC 14579 (AE017013), *Bacillus cereus* E33L (CP00001), *Bacillus licheniformis* ATCC 14580 (CP000002), *Bacillus licheniformis* DSM 13 (AEO 17333), *Bacillus subtilis* acetate kinase (L 17320), *Bacillus subtilis* rrnB-dnaB (AF008220), *Bacillus subtilis* subsp. *subtilis* str. 168 (Z99119) *Bacillus thuringiensis* serovar konkukian str. 97-27 (AE017355), *Clostridium acetobutylicum* ATCC 824 (AE007683), *Clostridium acetobutylicum* (U38234), *Staphylococcus aureus* MSSA476 (BX571857), *Staphylococcus aureus* subsp. aureus COL (CP000046), *Staphylococcus aureus* subsp. aureus Mu50 DNA (BA000017), *Staphylococcus aureus* subsp. aureus MW2 DNA (BA000033), *Staphylococcus aureus* subsp. aureus N315 (BA000018), and *Staphylococcus aureus* subsp. aureus MRSA252 (BX571856), and mixtures thereof.

3. A PCR amplification method for quantification of acetic acid-producing bacteria comprising amplifying a nucleic acid of an acetic acid-producing bacteria in the presence of forward primers selected from the group consisting of SEQ ID NO: 1 and SEQ ID NO: 2 and mixtures thereof and reverse primers selected from the group consisting of SEQ ID NO: 3 and SEQ ID NO: 4 and mixtures thereof.

4. The PCR amplification method of claim 3, wherein said forward primers and said reverse primers comprise oligonucleotides selected from the ackA gene region of said acetic acid-producing bacteria.

5. The PCR amplification method of claim 3, wherein nucleic acid produced by said method is quantified using a SYBR Green I dye.

6. The PCR amplification method of claim 3, wherein said acetic acid-producing bacteria is disposed in an environmental sample.

7. The PCR amplification method of claim 6, wherein said environmental sample is taken from at least one of a natural gas production operation and an oil production operation.

* * * * *

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
gcaccgcttc ayaatcc                                                 17

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
gcaccrcttc ayaaccc                                                 17

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gtttggtgga atgctgtatc                                              20

<210> SEQ ID NO 4
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 4
gtttgatgga atgcygtatc                    20